United States Patent [19]

Kaneko

[11] Patent Number: 4,768,676

[45] Date of Patent: Sep. 6, 1988

[54] CONTAINER FOR VOLATILE LIQUID AROMATICS

[75] Inventor: Toshihiko Kaneko, Higashi-Murayama, Japan

[73] Assignee: S.T. Chemical Co., Ltd., Tokyo, Japan

[21] Appl. No.: 129,174

[22] Filed: Dec. 7, 1987

[30] Foreign Application Priority Data

Dec. 8, 1986 [JP] Japan .......................... 61-188910[U]
May 11, 1987 [JP] Japan ............................ 62-69949[U]

[51] Int. Cl.$^4$ .............................................. A61L 9/12
[52] U.S. Cl. ................................... 220/267; 206/0.5; 239/44
[58] Field of Search ............... 206/0.5, 581, 229, 823, 206/205; 239/34, 44; 220/267

[56] References Cited

U.S. PATENT DOCUMENTS

| | | | |
|---|---|---|---|
| 1,135,124 | 4/1915 | Maas | 239/44 |
| 1,272,275 | 7/1918 | Klein | 239/44 |
| 1,818,684 | 8/1931 | Blechman | 239/44 |
| 3,633,881 | 1/1972 | Yurdin | 239/44 |
| 4,286,754 | 9/1981 | Jones | 239/44 |
| 4,374,571 | 2/1983 | Hirvela | 206/0.5 |
| 4,549,693 | 10/1985 | Barlics | 206/0.5 |
| 4,621,768 | 11/1986 | Lhoste et al. | 239/44 |

Primary Examiner—Joseph Man-Fu Moy
Attorney, Agent, or Firm—Burns, Doane, Swecker & Mathis

[57] ABSTRACT

A container for volatile liquid aromatics to perfume the air is disclosed, in which a cylindrical tube having a closed lower end and accomodating the absorbing core portion of a volatilizing structure extends downward from the top of the container into liquid aromatics stored in the main container body. Thus, the volatilizing structure is kept dry prior to use. The container also comprises an opener for the lower end of the tube receiving the absorbing core portion of the volatilizing structure. The opener may consist of a needle-shaped pin extending in the tube. Simple activation of the opener by the user of the container is sufficient to commence vaporization. The volatilizing portion of the volatilizing structure is preferably in the form of an elongated strip whose widthwise direction is vertically disposed and which is curved lengthwise into a fold.

15 Claims, 8 Drawing Sheets

CONTAINER FOR VOLATILE LIQUID AROMATICS

BACKGROUND OF THE INVENTION

1. Field of the Invention

The present invention relates to containers for volatile liquid aromatics which can be placed in locations such as bath rooms, sitting rooms, and bed rooms for volatilizing sweet-smelling liquid substances, hereinafter referred to as volatile liquid aromatics.

2. Description of the Prior Art

Containers for pleasantly odorous substances hereinafter referred to as aromatics, which store a quantity of liquid aromatics and are placed in bath rooms, bed rooms, sitting rooms, offices, etc., for perfuming the air by volatilizing the aromatics, are widely used. Such containers generally comprise an absorbent core member and a volatilizing member having a large area: the absorbent member absorbs the liquid aromatic stored in the container and leads it up to the volatilizing member; the volatilizing member volatilizes the aromatic into the room and gives off a sweet-smelling scent.

In the case of conventional containers for storing and volatilizing liquid aromatics, the absorbent member is immersed in the liquid aromatic even before the container is placed in a room and put into an operative condition. Thus, a separating member is interposed between the absorbent and the volatilizing member to prevent the volatilization and consumption of the liquid aromatic during the distribution stage or before it is put to use; when the container is put into an operative condition, the separating member is removed by the user. The removal of the separating member is effected as follows. First, the carrier of the volatilizing member is unscrewed from the main body of the container; next, the separating member is removed; lastly, the carrier of the volatilizing member is screwed back onto the main body of the container, so that the absorbent and the volatilizing member can come into mutual contact and the liquid aromatic can be led up to the volatilizing member through the absorbent member.

Thus, conventional containers have had the disadvantage that the separating member, which separates the volatilizing member from the absorbent member during the distribution stage, must first be removed by the user before it is put into operative condition. This removing operation is troublesome to the user. Therefore, there is a desire for containers which are less troublesome to use.

Conventional liquid aromatic containers have further disadvantages resulting from the geometry of the volatilizing portion of the absorbing and volatilizing structure, as explained below.

In conventional containers for liquid aromatics, the volatilization of the aromatic is effected by the combination of an absorbent core member and a volatilizing scent-storing member having a large area. The absorbent core member draws up the liquid aromatic to the top of the container; the volatilizing scent-storing member, which has a comparatively large area to ensure that an adequate amount of aromatics is volatilized therefrom, volatilizes the liquid aromatics led up to it through the abosorbent core member.

Conventional volatilization structures used in liquid aromatic containers include a variety of types. Japanese Utility Model Publication No. 56-16968, for example, teaches a volatilizing member having the form of a flat plate placed in a horizontal attitude which is abutted against the top of a vertical absorbent core member. Japanese Utility Model Publication No. 57-42435, on the other hand, discloses a volatilizing structure in which the absorbent core member and the volatilizing scent-storing member are formed as one integral body, by means, for example, of blanking, the volatilizing scent-storing portion being bent at the top of the absorbent core portion to extend horizontally. Furthermore, Japanese Utility Model Publication No. 62-2051 teaches a structure in which the volatilizing scent-storing member is kept in a vertical attitude.

In the case of the volatilizing structures as described above used in conventional containers for volatile liquid aromatics, the liquid aromatics stored in the container is led up to the volatilizing scent-storing member through the absorbent core and is diffused through the volatilizing scent-storing member to be volatilized therefrom into the air. The quantity of volatilized liquid aromatic depends on factors such as the efficacy of the absorbing core and the volatilizing scent-storing member with respect to their absorbing function and the effective volatilizing area of the volatilizing scent-storing member.

With respect to the volatilized quantity, it is essential to ensure that an appropriate quantity is volatilized according to the condition of use. It is also necessary to ensure that a predetermined amount of liquid aromatic keeps on being volatilized throughout entire period during which the aromatic is consumed.

On the other hand, the liquid aromatics which are used in the containers as described above contain coloring dyes and non-volatile solvents. These non-volatile materials are also led up through the absorbent core to the volatilizing scent-storing member together with the effective aromatic dissolved in the solvent. The volatile components are volatilized therefrom, while the non-volatile components left in the volatilizing scent-storing member are dissolved in the solvent continually supplied from the absorbent core, and are carried by the flow of the diffusing solvent to the portions furthest from the portion connected to the absorbent core. Thus, the non-volatile components concentrate and set on the volatilizing surface furthest from the absorbent core member, on which the concentration of non-volatile components continuously increases while that of the solvent components is continuously decreased.

Thus, the surfaces of the peripheral portions of the volatilizing scent-storing member are gradually coated by the setting non-volatile components, and the volatilization of the liquid aromatics is inhibited in such coated portions. The high-concentration areas of non-volatile components move gradually toward the central portions of the volatilizing scent-storing member; the coating of the surface thereof by the setting non-volatile components advances further toward the center of the volatilizing scent-storing member. Thus, a large area of the volatilizing surface is eventually covered by the setting non-volatile components, greatly reducing the quantity of volatilized liquid aromatics, as compared with the case at the initial stage of usage.

The remnant non-volatile components in the peripheral surfaces of the volatilizing scent-storing member can be observed visually in the form of the colored spots which are formed on the surface of the volatilizing scent-storing member by the accumulating dyes in the course of usage.

SUMMARY OF THE INVENTION

Thus, an object of the present invention is to provide an improved container for volatile liquid aromatics which is free of the disadvantages of the conventional containers as described above.

More specifically, the object of the present invention is to provide a container for volatile liquid aromatics which can be put into an operative condition by a simple and easy procedure, but which remains securely sealed prior to use.

Another object of the present invention is to provide a container for volatile liquid aromatics which can sustain a sufficient quantity of volatilization of the liquid aromatic throughout the use thereof until the aromatic is consumed.

Thus, according to the present invention, a container for volatile liquid aromatics is provided which comprises a hollow cylindrical tube in the main body of the container storing the liquid aromatic. The hollow cylindrical tube receives therein the elongated absorbing core portion of an absorbing and volatilizing member, and prevents it from being immersed in the liquid aromatic contained in the main body. The absorbing and volatilizing member includes, besides the elongated absorbing portion extending into the hollow cylindrical tube, a volatilizing portion which is operatively connected to the absorbing portion through an opening or a slit which is formed in the upper end of the hollow cylindrical tube.

The container according to the present invention also comprises an opener means which can be operated by the user of the container to rupture the lower end of the hollow cylindrical tube. The liquid aromatic stored in the main body is introduced into the tube through the rupture formed in the lower end of the tube, and the absorbing core portion of the absorbing and volatilizing member is immersed in the liquid aromatic.

In a preferred embodiment of the present invention, the lower end opener means of the hollow cylindrical tube comprises a needle-shaped member or pin with a pointed lower end. The upper end of the pin extends through another opening formed in the upper end of the hollow cylindrical tube, and is pushed down by the user to force the pointed lower end thereof through the lower end of the hollow cylindrical tube. Thus, a rupture is formed in the lower end of the tube to allow the liquid aromatic to enter therethrough, and the liquid aromatic wets the absorbing core and is led up to the volatilizing portion of the absorbing and volatilizing member.

There are a variety of other forms of the lower end opener of the hollow cylindrical tube which may be used in preferred embodiments of the present invention. Their details are described hereinbelow in connection with the preferred embodiments.

For the purpose of sustaining sufficient quantity of volatilization over a long period, the volatilizing portion of the absorbing and volatilizing member may comprise an elongated strip or band of an absorbent material. This volatilizing strip is preferably folded, such as into the shape of a circle, a rectangle, or a spiral and is disposed with its widthwise direction being vertically oriented. The connection of the volatilizing portion of the absorbing and volatilizing member to the absorbing portion thereof is effected at one point of the strip along the length of the strip.

The distance along the length of the strip between the regions of high concentrations of non-volatile material and those regions around the connection to the absorbing portion of the absorbing and volatilizing member, to which the solvent is continuously supplied and from which the solvent diffuses to other regions of the volatilizing strip, ensures that the progress of the gradual coating of the strip by the setting non-volatile components at the high-concentration regions of non-volatile components leaves a sufficient area for vaporization during the whole period of usage. Furthermore, due to the vertical attitude of the strip which exposes both main surfaces of the strip to the ambient air, a large area of vaporization is obtained by a relatively small strip. Thus, the relatively small volatilizing strip according to the present invention is capable of sustaining sufficient vaporization throughout a long period of use until the aromatic is completely consumed.

BRIEF DESCRIPTION OF THE DRAWINGS

Further details of the present invention are described below, with reference to the embodiments illustrated in the attached drawings, in which.

In the drawings, like reference numerals represent like or corresponding elements or portions.

Figure 1:
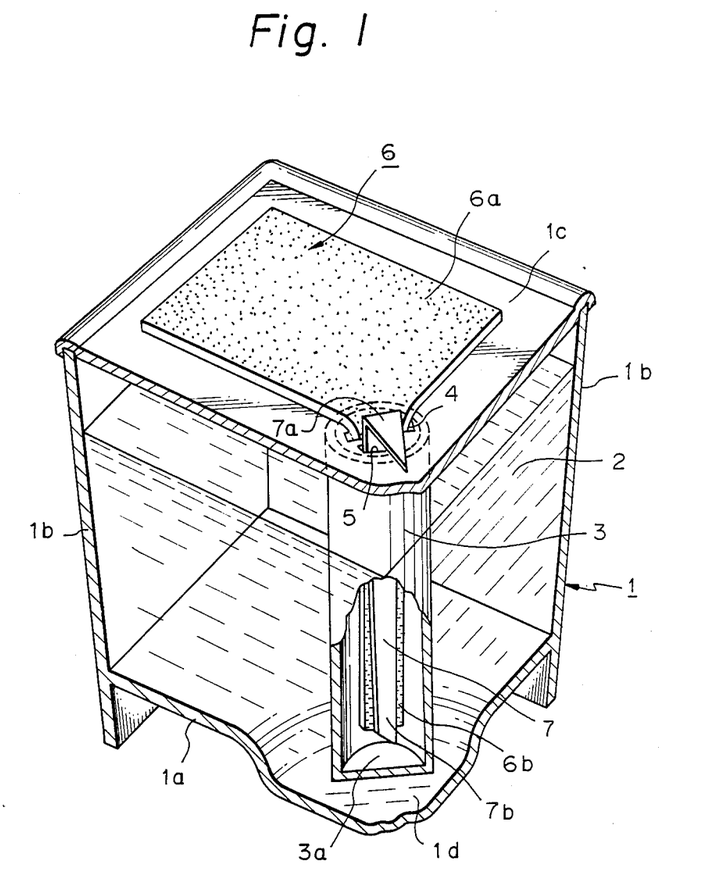
FIG. 1 is a cut-away perspective view of an embodiment of the container for volatile liquid aromatics according to the present invention.
Figure 2:
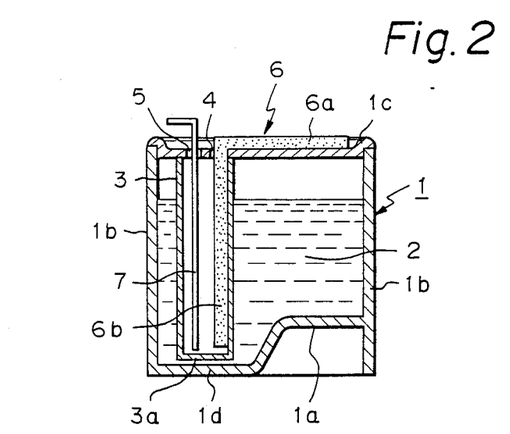
FIG. 2 is a vertical cross-sectional view of the embodiment of FIG. 1.

A first embodiment of the container according to the present invention, shown in FIGS. 1 and 2, comprises a main body 1 consisting of a rectangular bottom 1a, four side walls 1b, and a top plate 1c. The container main body 1, which is made, for example, of a thermoplastic synthetic resin such as polyethylene and polypropylene, stores a quantity of volatile liquid aromatic 2 in a hermetically sealed state. A depression 1d is formed in one corner of the bottom plate 1a. The liquid aromatic 2 may comprise aromatic substances, solvents, and dyes. Examples of aromatic substances include those of fruit or flower flavor; solvents may comprise surface active agents for promoting the solution of aromatic substances, together with a small quantity of ethanol.

A hollow cylindrical tube 3, having a closed end 3a which confronts the depression 1d, and made, for example, of a thermoplastic synthetic resin such as polyethylene and polypropylene, extends vertically in the main body 1 and is fixed to the top plate 1c of the main body 1 of the container at the upper end thereof. Thus, in the pre-use condition illustrated in FIGS. 1 and 2, the liquid aromatic 2 stored in the main body 1 is excluded from the interior of the tube 3.

An absorbing and volatilizing member 6, made of a flat absorbent material such as felt, non-woven fabric, or filter paper, comprises a strip-shaped elongated absorbing core portion 6b and a flat volatilizing portion 6a having a large area. The elongated absorbing portion 6b extends vertically through the tube 3, and is connected to the volatilizing portion 6a through an opening or a slit formed at the upper end of the tube 3 in the top plate 1c of the main body 1. The volatilizing portion 6a having a rectangular volatilizing area placed upon the top plate 1c of the main body 1 is formed of an absorbent material such as felt and is integral with the absorbing portion 6b. It is bent into a horizontal attitude at the opening 4 at the upper end of the tube 3. The perferred absorbent materials which may be utilized for the absorbing and volatilizing member 6 include felt, non-woven fabric, and filter paper.

A flat needle-shaped pin 7 having a pointed lower end also extends vertically within the hollow cylindrical tube 3. The upper end of the pin 7 which extends through an opening 5 and has a form corresponding to the cross-section of the pin 7 is bent in the horizontal direction to form a pin head 7a. The pin 7 is made, for example, of a thermoplastic synthetic resin such as polyacetals, or a metal.

Thus, as shown in the figures the absorbing portion 6b of the absorbing and volatilizing member 6 remains dry prior to use since the liquid aromatics stored in the main body are prevented from being introduced into the hollow tube 3 as long as the lower end 3a thereof remains closed.

When the container is to be put into operation, the pin head 7a is pushed down by the user to slide the pin 7 down through the slit 5 in the tube 3. The pointed lower end 7b thereof is then forced through the lower end 3a to form a hole therein. The liquid aromatic 2 is thus introduced into the interior of the tube 3 and the absorbing portion 6b of the absorbing and volatilizing member 6 becomes immersed in the liquid aromatic 2. The liquid aromatic is thus led up to the volatilizing portion 6a of the absorbing and volatilizing member 6 through the absorbing portion 6b thereof and is volatilized therefrom into the ambient air.

Thus, simply pushing the pin head 7a down is sufficient to commence the volatilization of the liquid aromatic 2 hermetically stored in the container main body 1. Furthermore, the depression 1d in the bottom 1a of the main body 1 accumulates the liquid aromatics 2 remaining in the main body 1 at the last stage of its usage, so that all the liquid aromatics stored in the body 1 can be vaporized to the last drop.

Figure 3:
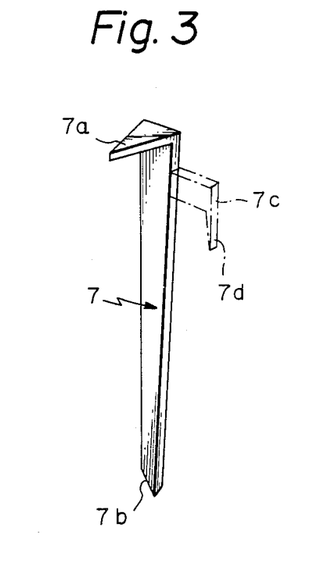
FIG. 3 is a perspective view of a needle-shaped pin which may be employed in the container of FIG. 1.

FIG. 3 shows an embodiment of the pin 7 which may be utilized in the container shown in FIGS. 1 and 2. The pin may include a hook-shaped member 7c as shown by the dot and dash line which is formed integrally on a side surface of the pin 7 near the pin head 7a. When the pin 7 is inserted into the tube 3 through the slit 5, the hook 7c extends over the top plate 1c of the main body 1 above the tube 3. When the pin head 7a is pushed down to commence the vaporization, the pointed needle portion 7d of the hook 7c opens a ventilating hole in the top plate 1c. Thus, air can pass through the upper end of the tube 3 through the ventilating hole thus formed by the needle 7d of the hook 7c.

Figure 4:
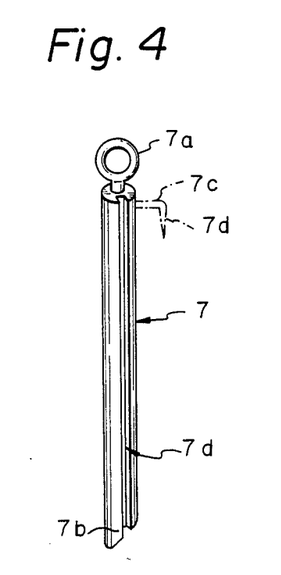
FIG. 4 is a perspective view of another needle-shaped pin.

FIG. 4 shows another embodiment of the pin 7 which may be utilized in a container of liquid aromatics according to the present invention similar to that of FIGS. 1 and 2. The pin 7 of this figure has a cylindrical shape with a pointed lower end 7b. The pin head 7a has the form of a ring attached to the top of the cylinder. A hook-shaped member 7c similar to that of FIG. 3 for opening a ventilating hole may also be provided on the side surface of the cylinder of the pin 7 near the top thereof. Furthermore, a vertically extending groove 7d is formed on the side surface of the cylinder of the pin 7. When positioned in the tube 3, the groove 7d faces the absorbing portion 6b of the absorbing and volatilizing member 6 shown in FIGS. 1 and 2 so that the liquid aromatics are led up therethrough by means of capillary action.

Figure 5:
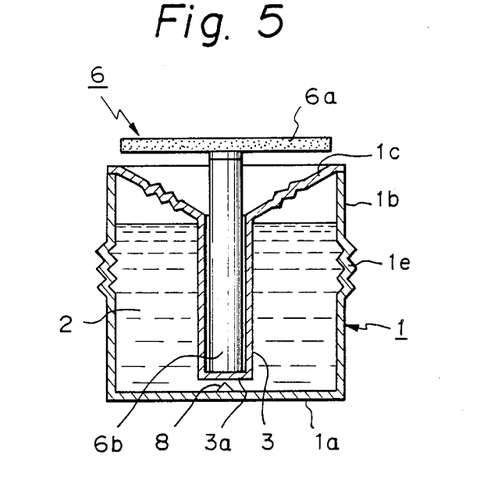
FIG. 5 is a vertical cross-sectional view of another embodiment of the container according to the present invention.

A second embodiment of the container according to the present invention shown in FIG. 5 comprises a main body 1 the side walls 1b of which has a portion formed into bellows 1e having a zigzag cross-section, so that the main container body 1 itself can be contracted in the vertical direction. The body 1 of this embodiment may be made of a thermoplastic synthetic resin such as polyethylene and polypropylene. The top 1c of the main body 1 is formed into a funnel-shape. The hollow cylindrical tube is integral with the center of the funnel-shaped portion and extends downward therefrom. The absorbing portion of the absorbing and volatilizing member 6 has the form of a cylindrical core 6b made of an absorbent material extending through the interior of the cylindrical tube 3. The volatilizing portion 6a of the absorbing and volatilizing member 6 has the form of a plate or a disk formed of an absorbent material which is abutted to the upper end of the absorbing core 6b at the central portion thereof. A pointed projection 8 is formed on the bottom 1a of the main body 1 to confront the closed end 3a of the cylindrical tube 3.

To put the container of FIG. 5 into an operative condition, the volatilizing plate or disk 6a of the absorbing and volatilizing member 6 is pushed down by the user. Due to the contraction of the bellows 1e in the side walls 1b of the main body 1, the cylindrical tube 3, which is pushed downward at the lower closed end 3a by the lower end of the core 6b moves downward toward the bottom plate 1a of the main body 1. Thus, the pointed projection 8 on the bottom 1a of the main body 1 ruptures an opening in the closed lower end 3a of the cylindrical tube 3, thereby letting the liquid aromatic 2 stored in the main body 1 of the container into the interior of the cylindrical tube 3. The liquid aromatic 2 thus introduced into the tube 3 is absorbed by the core 6b and led up therethrough to the volatilizing plate or disk 6a. The liquid aromatic is then vaporized therefrom. The body 1 is made, for example, of a thermoplastic synthetic resin such as polyethylene and polypropylene, while the projection 8 is made, for example, of a thermoplastic synthetic resin such as polyacetals, or a metal.

Figure 6:
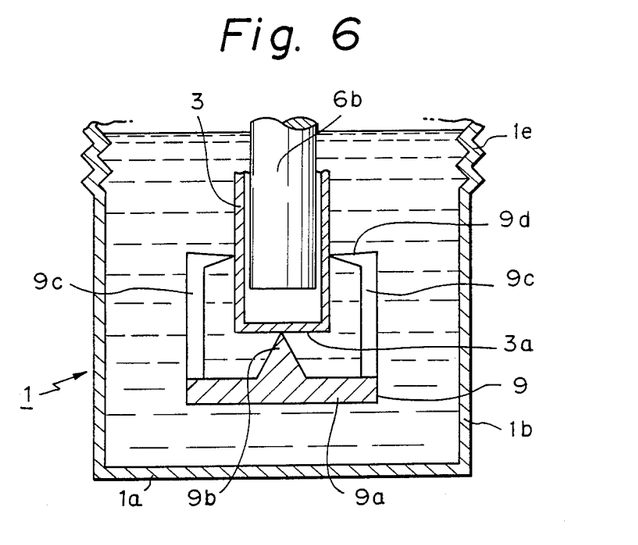
FIG. 6 is a view similar to that of FIG. 5, but showing a lower portion of still another embodiment of the container according to the present invention.

FIG. 6 shows another embodiment which except for the illustrated portions similar to that shown in FIG. 5. This embodiment further comprises an inverted crown 9 which is fitted on the lower end portion of the cylindrical tube 3 from below. The upper surface of the bottom 9a of the inverted crown 9 has formed thereon a projection 9b which confronts the lower end 3a of the cylindrical tube 3. The crown 9 is secured to the tube 3 by means of a plurality of side posts 9c extending upward from the bottom of the crown and each having a horizontally projecting nail 9d to engage with the outer side surface of the tube 3. Thus, a sufficient gap is left between the side posts 9c and between the outer surface of the tube 3 and the inner surfaces of the inverted crown 9. The crown 9 is made, for example, of a thermoplastic synthetic resin such as polyacetals, or a metal.

The volatilization of the container of FIG. 6 is commenced as follows. When the volatilizing plate similar to that 6a of FIG. 5 attached to the top of the core 6b is lowered and forces the lower end of the core 6b against the closed lower end 3a of the tube 3, the inverted crown 9 is pushed against the bottom plate 1a of the main body 1, together with the lower end 3a of the tube 3. Thus, the pointed projection 9b is forced through the lower closed end 3a of the tube 3 to form a rupture therein, and the volatilization of the aromatics 2 follows by a process similar to that described above.

Figure 7:
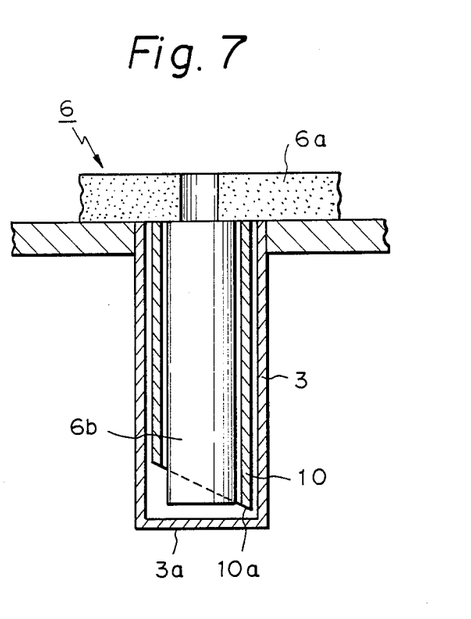
FIG. 7 is a vertical cross-sectional view of a portion of still another embodiment of the container according to the present invention, showing the neighborhood of the absorbing core thereof.

FIG. 7 shows a central portion of a fourth embodiment of the container according to the present invention. In the case of this fourth embodiment, the opener of the closed lower end of the cylindrical tube 3 consists of a hollow cylinder 10 having a slanted and pointed lower end 10a. The cylinder 10 is fixed to the volatilizing plate 6a of the absorbing and volatilizing member 6 at the upper end thereof, and extends downward through the tube 3 coaxially around the cylindrical absorbing core 6b of the absorbing and volatilizing member 6. The structure of this embodiment is otherwise similar to that of the embodiment of FIG. 5.

The pointed lower end 10a of the cylinder 10 is close to or in virtual contact with the lower end 3a of the tube 3.

The commencement of the vaporization is performed in a manner similar to those described in conjunction with the embodiments of FIGS. 5 and 6. First, volatilizing plate 6a of the absorbing and volatilizing member 6 is pushed down. The portion shown in FIG. 7 moves downward toward the bottom of the main container body due to the contraction of the side walls thereof due to the bellows structure. Thus, the pointed lower end 10a of the cylinder 10 is forced against the closed end 3a of the tube 3, and a hole is formed in the closed end 3a of the tube 3 by the pointed lower end 10a of the cylinder 10 to allow the liquid aromatics into the interior of the tube 3.

Figure 8:
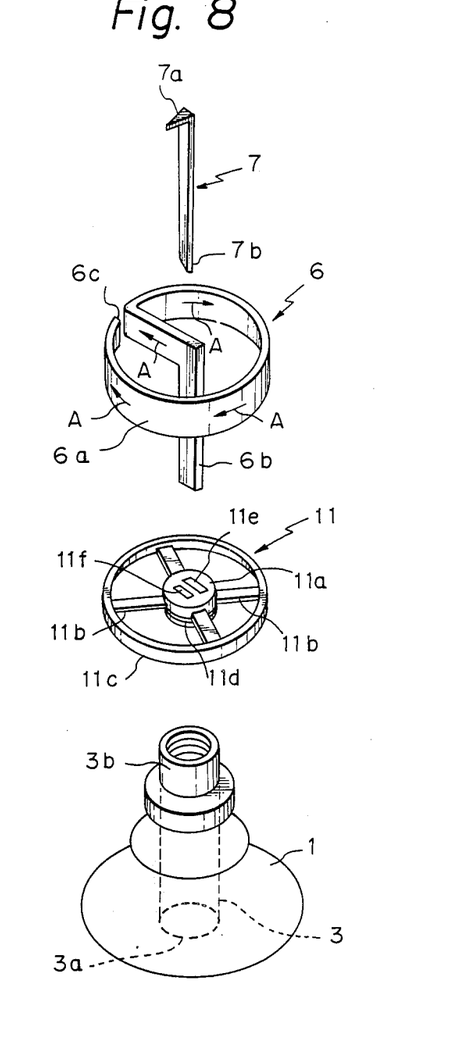
FIG. 8 is an exploded perspective view of still another embodiment of the container according to the present invention.

FIG. 8 is an exploded view of a fifth embodiment of the container according to the present invention. This embodiment has a structure similar to that of the first embodiment shown in FIGS. 1 and 2, and is operated similarly, except for those differences that are described below.

A container main body 1 having rotational symmetry has disposed therein a cylindrical tube 3 having a closed lower end 3a. The upper end portion of the tube 3b extends out of the main body 1, and has an interior side surface on which a female thread 3c is formed.

The carrier 11 of the absorbing and volatilizing member 6, is made, for example, of a thermoplastic synthetic resin such as polyethylene and polypropylene. It comprises a hub 11a, a circumferential ring 11c, and ribs 11b connecting the hub 11a and the ring 11c, all of which are integral with one another. The lower portion of the hub 11a has formed on the side surface thereof a male thread 11d which is screwed into the thread 3c of the tube 3. Slits 11e and 11f, having cross-sections which match those of the absorbing portion 6b of the absorbing and volatilizing member 6 and the pin 7, respectively, extend vertically through the hub 11a.

The absorbing and volatilizing member 6, made of an absorbent material such as felt, comprises a volatilizing strip 6a and a absorbing portion 6b. The strip 6a is formed as one integral body with the absorbing portion 6b and is bent and curved along its length into a circle to fit within the circumferential ring 11c of the carrier 11.

The pin 7 has a form similar to that of the pin shown in FIGS. 1 and 2.

When the pin is operated to form a hole in the lower end 3a of the tube 3 so that the liquid aromatic stored in the body 1 is introduced into the tube 3, the solvent flows in the longitudinal direction A of the strip 6a and eventually is led to the end 6c of the circle formed by the strip 6a. Thus, the non-volatile components which are carried by the flow of the solvent concentrate and set at the end 6c of the circle of the strip 6a. Therefore, the coating of the volatilizing strip 6a by the setting non-volatile components contained in the liquid aromatic advances from the region which is removed furthest from the connection to the absorbing portion 6b. Furthermore, the erect or vertical attitude of the volatilizing strip 6a exposes both main surfaces of the strip 6a to the ambient air, thereby obtaining a large area of volatilization, in spite of the relative smallness of the volatilizing strip 6a.

FIGS. 9 through 17 shows further examples of the absorbing and volatilizing member which may be disposed in a container for liquid aromatics similar to that shown in FIG. 8. The form of the main body 1 and the carrier 11, and the position of the cylindrical tube 3 receiving the absorbing portion 6b of the absorbing and volatilizing member 6 as illustrated in FIG. 8 may also be modified according to the particular form of the volatilizing strip 6a and the location of the connection thereof to the absorbing portion 6b illustrated in FIGS. 9 through 17, as will be easily understood by those skilled in the art.

Figure 9:
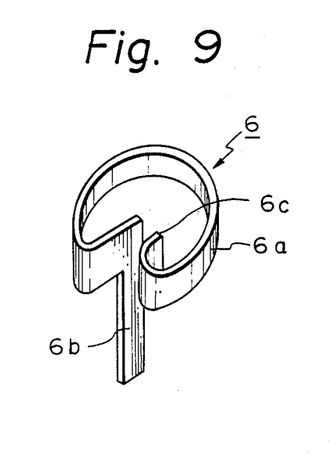
FIGS. 9 through 17 are perspective views of the absorbing and volatilizing members according to the present invention, showing various forms thereof.
Figure 10:
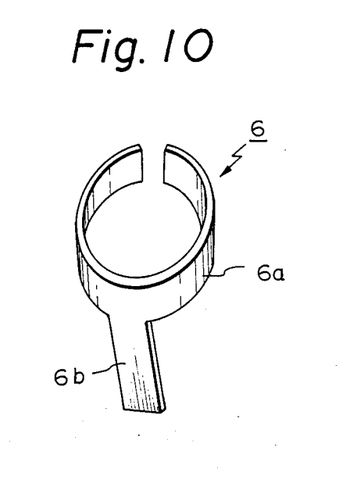
Figure 11:
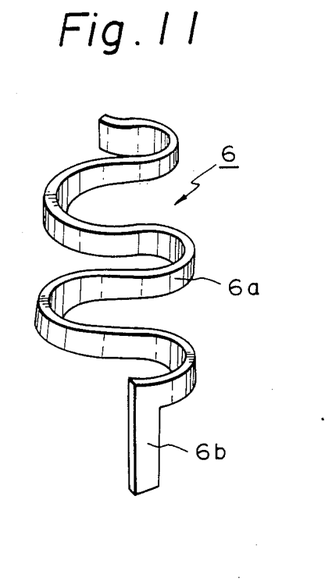
Figure 12:
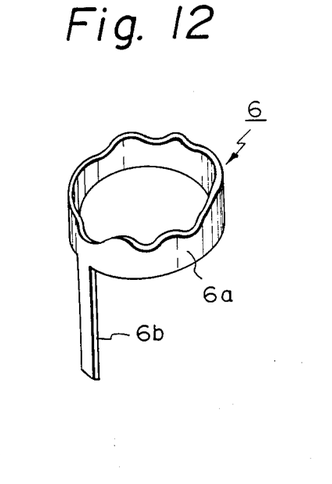
Figure 13:
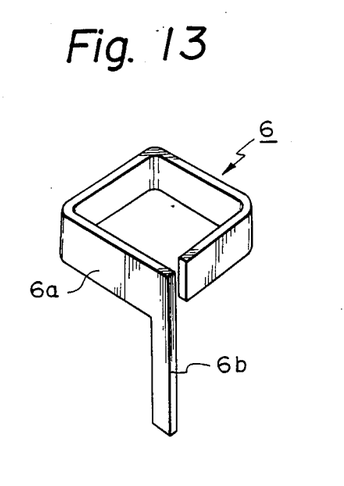
Figure 14:
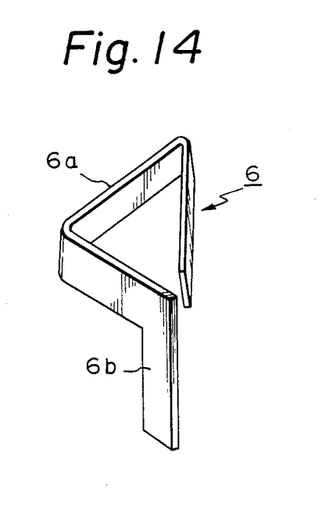
Figure 15:
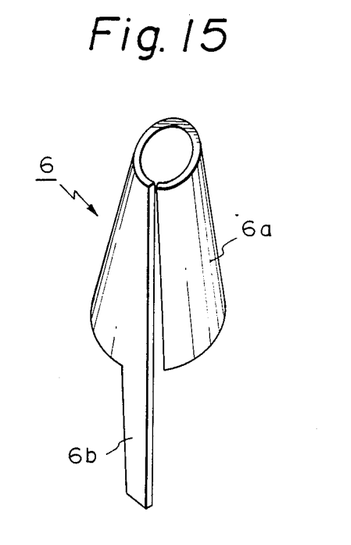

FIG. 9 shows a form of the absorbing and volatilizing member 6 in which the volatilizing strip 6a has a circular form similar to that of the strip 6 shown in FIG. 8, but the end 6c is further bent toward the interior of the circle of the strip 6a. FIG. 10 shows the case in which the absorbing portion 6b is connected to the circular volatilizing strip 6a midway along the length thereof. FIG. 11 shows a volatilizing strip 6a which is curved into an undulating shape, at one end of which the absorbing portion 6b is connected. FIG. 12 shows a volatilizing strip 6a which has the form of a complete circle or a ring having an undulating upper edge. FIG. 13 shows a volatilizing strip 6a having the form of a rectangle. FIG. 14, on the other hand, shows a strip 6a having the form of a triangle. FIG. 15 shows a volatilizing strip 6a which has a large width and is curved into the shape of a hollow cone.

Figure 16:
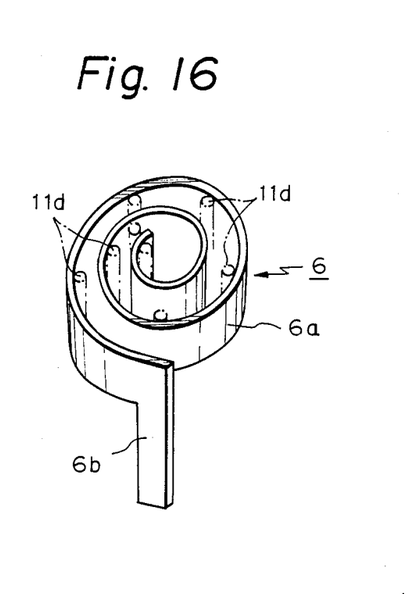
Figure 17:
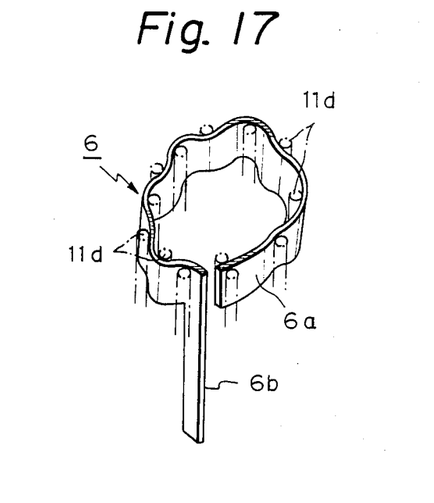

In the cases shown in FIGS. 16 and 17, the volatilizing strip 6a of the absorbing and volatilizing member 6 is securely held between a plurality of small posts 11d which are fixed uprightly on the bottom plate (not shown) of a carrier which is similar to the carrier 11 of FIG. 8, but comprises a bottom plate. The strip 6a shown in FIG. 16 has the form of a coil or an involute.

The strip 6a shown in FIG. 17, on the other hand, has an undulating circular form.

In all the examples illustrated in FIGS. 9 to 17, the volatilizing strip 6a is disposed with its widthwise direction being vertically oriented to ensure a large area of exposure to the air and volatilization, and is folded along its length so as to have relatively small dimensions. Furthermore, the absorbing core is connected to the volatilizing strip at a location along the length of the strip such that the regions of the strip which are furthest from the connection are separated from the connection by a distance substantially not less than one half of the length of the strip. Thus, although the strip 6a can be accomodated in a relatively small carrier, a sufficient amount of volatilization can be sustained throughout the whole period of use of the container.

Figure 18:
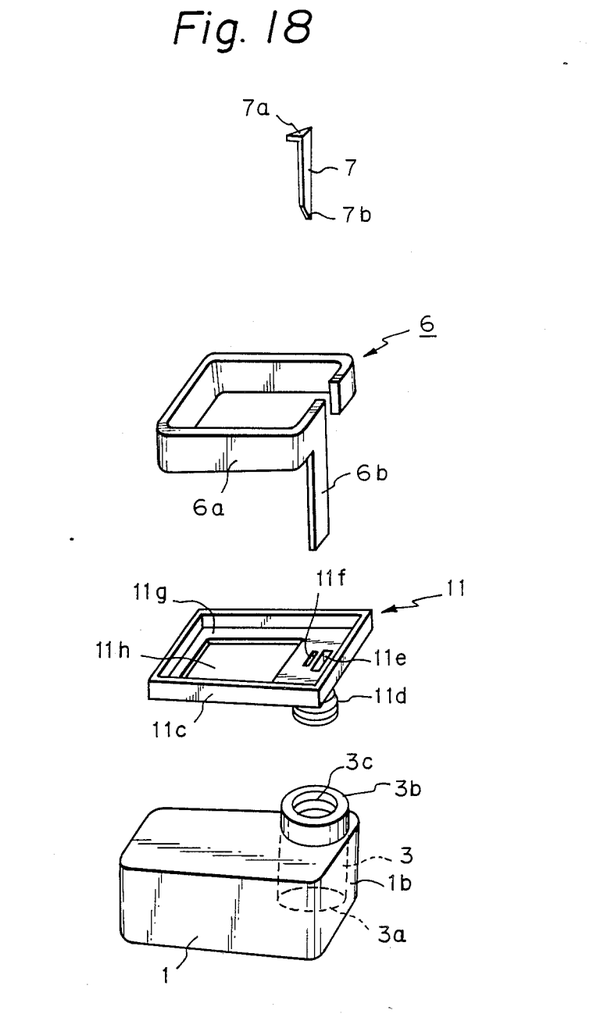
FIG. 18 is an exploded perspective view of still another embodiment of the container according to the present invention.

FIG. 18 shows a sixth embodiment of the container according to the present invention which is similar to that shown in FIG. 8, except for the points which are described below.

The main body 1 has the form of a rectangular parallellopiped. The tube 3 receiving the absorbing portion 6b of the absorbing and volatilizing member 6 is situated near a side wall 1b of the main body 1. The carrier 11 of the absorbing and volatilizing member 6 has the form of a rectangular plate with side ridges 11c and a bottom plate 11g which has a central opening 11h. A male thread 11d is formed on a hollow cylindrical projection extending downward at a position corresponding to that of the upper end portion 3b of a tube 3, which has a female thread 3c formed on the interior surface thereof. The pin 7 and the absorbing and volatilizing member 6 are fitted through the slits 11d and 11f, respectively, which are formed in the bottom 11g of the carrier 11.

What is claimed is:

1. A container for volatile liquid aromatics for storing and volatilizing liquid aromatics, comprising:
    a main container body means for storing a quantity of volatile liquid aromatic;
    a hollow cylindrical tube having a closed lower end and extending vertically downward from a top of said main container body means into an interior of said main container body means;
    an absorbing and volatilizing member including an elongated absorbing portion extending into said hollow cylindrical tube and a volatilizing portion connected with said elongated absorbing portion through an opening in an upper end of said hollow cylindrical tube; and
    lower end opener means for opening a hole in said closed lower end of said hollow cylindrical tube to introduce the liquid aromatics stored in said main container body means into an interior of said hollow cylindrical tube, thereby letting the liquid aromatic be absorbed by said absorbing portion of said absorbing and volatilizing member and be volatilized by said volatilizing portion of said absorbing and volatilizing member.

2. A container for volatile liquid aromatics as claimed in claim 1, wherein said lower end opener means comprises a needle-shaped member having a pointed lower end disposed in said hollow cylindrical tube, an upper end of said needle-shaped member slidably extending through an opening in the upper end of said hollow cylindrical tube, said pointed lower end of the needle-shaped member directed downward toward the lower end of the cylindrical tube in proximity thereto.

3. A container for volatile liquid aromatics as claimed in claim 2, wherein said container further comprises air communicating means for forming an opening in said upper end of hollow cylindrical tube thereby establishing air communication between an interior and an exterior of said hollow cylindrical tube through said upper end, said air communicating means comprising a needle integral with said needle-shaped member of lower end opener, said needle comprising means for opening a hole in said upper end of said hollow cylindrical tube when said needle-shaped member means is lowered to open a hole in said closed lower end of said hollow cylindrical tube.

4. A container for volatile liquid aromatics as claimed in claim 1, wherein said lower end opener means comprises means for leading up the liquid aromatic through said hollow cylindrical tube.

5. A container for volatile liquid aromatics as claimed in claim 4, wherein said means for leading up the liquid aromatics comprises means for leading up the liquid aromatic through said hollow cylindrical tube by means of capillary action.

6. A container for volatile liquid aromatics as claimed in claim 5, wherein said elongated absorbing portion of said absorbing and volatilizing member comprises a solid cylinder made of an absorbent material, and said lower end opener means comprises a hollow cylinder having a pointed lower end, said hollow cylinder being disposed coaxially with said solid cylinder to form a narrow gap between an outer side surface of said solid cylinder and an inner side surface of said hollow cylinder, the gap leading up the liquid aromatic by capillary action.

7. A container for volatile liquid aromatics as claimed in claim 5, wherein said lower end opener means comprises a cylindrical member having a pointed lower end slidably disposed in said hollow tubular member, said cylindrical member having formed on an outer side surface thereof a groove extending in a longitudinal direction of said cylindrical member.

8. A container for volatile liquid aromatics as claimed in claim 1, wherein said lower end opener means comprises a pointed projection formed on a lower inner surface of said main container body means, said pointed projection confronting said closed lower end of said hollow tubular member.

9. A container for volatile liquid aromatics as claimed in claim 1, wherein said lower end opener means comprises an inverted crown having formed on an upper surface of a bottom thereof a pointed projection, said crown being slidably engaged upon said hollow cylindrical tube from below to form a gap around an outer surface of said hollow cylindrical tube to allow a flow of the liquid aromatic therethrough.

10. A container for volatile liquid aromatics as claimed in claim 1, wherein said absorbing and vaporizing member is made of an absorbent material.

11. A container for volatile liquid aromatics as claimed in claim 10, wherein said absorbent material is selected from the group consisting of felt, non-woven fabric, and filter paper.

12. A container for volatile liquid aromatics as claimed in claim 10, wherein said volatilizing portion of said absorbing and volatilizing member comprises an elongated strip of an absorbent material longitudinally curved into a fold, a widthwise direction of said elongated strip being vertically disposed, and wherein volatilizing regions of said elongated strip which are separated furthest from a connection of the strip which is connected to the elongated absorbing portion of the absorbing and volatilizing member are separated from said connection by a distance substantially not less than one half of a whole longitudinal lengthy of the strip.

13. A container for volatile liquid aromatics as claimed in claim 10, wherein said elongated absorbing portion and said volatilizing portion of said absorbing and volatilizing member are formed as one integral body.

14. A container for volatile liquid aromatics as claimed in claim 10, wherein said elongated portion and said volatilizing portion of said absorbing and volatilizing member are formed as separate bodies which are contacted by means of mutual abutment thereof.

15. A container for volatile liquid aromatics as claimed in claim 12, further comprising a carrier disposed on a top of said main container body on which said elongated strip of an absorbent material of the volatilizing portion of said absorbing and volatilizing member is positioned, said carrier comprising means for engaging with said elongated strip of absorbent material in a predetermined position.

* * * * *